United States Patent
Rosenbloom

(10) Patent No.: US 7,399,783 B2
(45) Date of Patent: Jul. 15, 2008

(54) METHODS FOR THE TREATMENT OF SCAR TISSUE

(75) Inventor: Richard A. Rosenbloom, Elkins Park, PA (US)

(73) Assignee: The Quigley Corporation, Doylestown, PA (US)

( * ) Notice: Subject to any disclaimer, the term of this patent is extended or adjusted under 35 U.S.C. 154(b) by 440 days.

(21) Appl. No.: 11/158,986

(22) Filed: Jun. 22, 2005

(65) Prior Publication Data

US 2006/0293257 A1    Dec. 28, 2006

(51) Int. Cl.
- *A01N 43/16* (2006.01)
- *A61K 31/35* (2006.01)
- *A01N 43/04* (2006.01)
- *A61K 31/70* (2006.01)

(52) U.S. Cl. .................... 514/457; 514/27; 514/449; 514/451; 514/453; 514/456

(58) Field of Classification Search ................ None
See application file for complete search history.

(56) References Cited

U.S. PATENT DOCUMENTS

| | | | | |
|---|---|---|---|---|
| 5,639,740 | A * | 6/1997 | Crandall | 514/78 |
| 5,928,659 | A | 7/1999 | Moy | |
| 6,753,325 | B2 * | 6/2004 | Rosenbloom | 514/167 |
| 7,083,813 | B2 * | 8/2006 | Rosenbloom | 424/725 |
| 2003/0049283 | A1 * | 3/2003 | Vandell | 424/401 |
| 2004/0151793 | A1 | 8/2004 | Paspaleeva-kuhn et al. | |

OTHER PUBLICATIONS

Mohamed Hany El-Tonsy, MD and Arthur C. Huntley, MD, Egyptian Dermatology Online Journal, 2005, Internet Web Page, pp. 1-3, vol. 1, No. 1, Published by Mohamed Hany El-Tonsy, MD, Egypt.
Maha F. El Goweini, MD and Nagwa M. Nour El Din, MD, Egyptian Dermatology Online Journal 1 (1):5: "Effect of Quercetin on Excessive Dermal Scarring," Internet Web Page, pp. 1-9, vol. 1, No. 1, 2004.
Toan-Thang Phan, MD, Li Sun, MD, Boon-Huat Bay, PhD, Sui-Yung Chan, PhD, and Seng-Teik Lee, FRCS, FAMS; The Journal of Trauma Injury, Infection and Critical Care, "Dietary Compounds Inhibit Proliferation and Contraction of Keloid and Hypertrophic Scar-Derived Fibroblasts In Vitro: Therapeutic Implication for Excessive Scarring," vol. 54, No. 6, pp. 1212-1224, Jun. 2003.
Phan, Toan-Thang MD, PhD; Lim, Ivor Jiun MD, FRCS; Chan, Sui-Yung PhD; Tan, Ee-Kim BSc; Lee, Seng-Teik MD, FRCS and Longaker, Michael T. MD, FRCS, The Journal of Trauma Injury, Infection and Critical Care, "Suppression of Transforming Growth Factor Beta/Smad Signaling in Keloid-Derived Fibroblasts by Quercetin: Implications for the Treatment of Excessive Scars," Internet Web Page, vol. 57(5); Nov. 2004.
Marilyn Sterling, R.D., Article: Science Beat, Internet Web Page, Natural Foods Merchandiser vol. XXIV, No. 10, p. 50, 2003.
Phan TT, See P, Tran E, Nguyen TT, Chan SY, Lee ST and Huynh H., Pub Med, Internet Web Page, "Suppression of Insulin-like Growth Factor Signalling Pathway and Collagen Expression in Keloid-Derived Fibroblasts by Quercetin: It's Therapeutic Potential Use in the Treatment and/or Prevention of Keloids," Br. J. Dermatol., Mar. 2003, 148(3):544-52.
Crystal Smith, Kevin A. Lombard, Ellen B. Peffley and Weixin Liu; "Genetic Analysis of Quercetin in Onion (*Allium cepa* L.) 'Lady Raider'," The Texas Journal of Agriculture and Natural Resource, vol. 16 pp. 24-28, 2003.
Skin Actives Scientific L.L.C., Internet Web Page, "Quercetin," Quercetin by Skinactives, printed on Apr. 10, 2006.
Saulis, Alexandrina S. M.D.; Mogford, Jon H. Ph.D.; Mustoe, Thomas A., M.D., Plastic and Reconstructive Surgery, "Effect of Mederma on Hypertrophic Scarring in the Rabbit Ear Model," Journal of the American Society of Plastic Surgeons, vol. 110, No. 1, pp. 177-183, Jul. 2002.
Ageless Herbal Products, "Herbal Stretch Mark Gel," Internet Web Advertisement, printed Apr. 11, 2006.
Advanced Stretch Marks Lotion with Top Firming Ingredients, "Stretch Marks Solved by Botanical Body," Internet Web Advertisement, printed Apr. 11, 2006.
WhatVitaminsareRightforYou.com; Stretch Marks; Internet Web pp. 1-4, 2004.
Removal Treatment for Stretch Marks, "StretchRenew.com"; Internet Web Advertisement, pp. 1-6, 1998.
Revitol: Stretch Mark Cream: Review; Stretch-Mark-Guide.com; Internet Web Advertisement, 1 page, printed Apr. 10, 2006.
Stretch Mark Solutions, Internet Web Page/Advertisement, 3 pages, Jan. 24, 2006.
Elliott Middleton, Jr., Chithan Kandaswami and Theoharis C. Theoharides, *The effects of Plant Flavnoids on Mammalian Cells: Implications for Inflammation, Heart Disease and Cancer*, vol. 52, Issue 4, 673-751, Dec. 2000.

* cited by examiner

*Primary Examiner*—Patrick T Lewis
(74) *Attorney, Agent, or Firm*—Knoble, Yoshida & Dunleavy, LLC

(57) ABSTRACT

A topical composition and method for the reduction of scar tissue and/or improving the appearance of scar tissue after it has formed. The topical composition includes one or more flavonoids formulated in a pharmaceutically acceptable topical carrier. The method includes the step of topically applying a composition including one or more flavonoids formulated in a pharmaceutically acceptable topical carrier to scar tissue to reduce the amount of, or improve the appearance of the scar tissue. The topical compositions and methods of the present invention reduce scar tissue after it has formed as well as improving the appearance of the remaining scar tissue.

14 Claims, No Drawings

METHODS FOR THE TREATMENT OF SCAR TISSUE

BACKGROUND OF THE INVENTION

1. Field of the Invention

The present invention relates to compositions and methods for the cosmetic treatment of scar tissue. More specifically, the method of the present invention, relates to the topical application of at least one flavonoid to scar tissue.

2. Brief Description of the Prior Art

Damage or injury to skin tissues and/or organs is a common occurrence. The body is most often able to isolate the damaged area and then repair itself by removing and replacing damaged tissue. Injury to tissues and organs can originate from a great variety of sources such as, for example, trauma, UV degradation, toxic and/or pathogenic degradation, thermal degradation (e.g. excessive heat or cold) and so forth. While the body has an impressive array of response mechanisms that limit tissue damage and promote repair, methods of increasing the speed and degree of repair are continually being sought out. Additionally, the presence of scar tissue can be unsightly, and the reduction of scar tissue is aesthetically desirable. In this regard, increasing the speed and/or degree that scar tissue is removed is beneficial in that it (i) decreases the visibility of unsightly tissue; (ii) decreases the chances of developing an infection or other ailment through re-injury of the scarred area or the surgical removal of scar tissue; and (iii) reduces health costs associated with treating such conditions.

Although compounds exist for promoting the healing of wounds, there exists a continuing need for additional and/or improved compounds for treating and/or reducing scar tissue.

Accordingly, it is an object of certain embodiments of the present invention to provide a composition that is effective for the treatment of scar tissue.

It is an object of other embodiments of the present invention to provide a method that is effective for the treatment of scar tissue

SUMMARY OF THE INVENTION

In a first aspect, the invention relates to a method for the reduction or treatment of scar tissue comprising the step of topically applying to scar tissue, a composition which comprises a therapeutically effective amount of one or more flavonoids.

In a second aspect, the invention relates to a topical composition for reduction of scar tissue comprising a therapeutically effective amount of a flavonoid, tangerine oil; hyaluronic acid, and a pharmaceutically acceptable carrier for a topical composition.

DETAILED DESCRIPTION OF THE PREFERRED EMBODIMENTS

The compositions and methods of the invention provide a reduction of scar tissue that has already formed or to improve the appearance of scar tissue. Reduction of scar tissue refers to the treatment of scar tissue to reduce the amount of scar tissue. For example, this can be measured by a reduction in the area or width of a scar. An improvement in the appearance of scar tissue can be evaluated on the basis of, for example, the scar scale evaluation that is presented below in the examples.

The treatment of the present invention is applied to scar tissue after the scar tissue has formed. This treatment includes application to scar tissue after complete healing of a wound, or application to scar tissue while the wound is still in the process of healing, e.g. application to already formed scar tissue that forms part of a healing wound.

The term "scar tissue" is used to refer to the connective tissue that forms a scar and which consists primarily of fibroblasts in new scars, and collagen fibers in older scars. Scar tissue is generally characterized by red discoloration, edema, irritation and dehiscence. Patients afflicted with scar tissue typically have visible indications of past wounds located on their skin.

The term "derivatives," as used herein, refers to structurally similar compounds that exhibit a common activity (e.g., antioxidant) and contain at least one significant, common structural element with the compound from which it is derived, which common structural element provides the common activity.

The expression "therapeutically effective amount," as used herein, refers to a nontoxic amount of a compound, which is sufficient to provide the desired therapy to promote the cosmetic improvement of scar tissue. A therapeutic amount may, for example, reduce the amount of scar tissue, or affect one or more characteristics of the scar tissue to thereby render the scar tissue less visible or noticeable. The exact amount required may vary, depending on the species, age, and general condition of the patient, the nature of the complications, the particular combination of compounds, the mode of administration, and the like.

As used herein, a "pharmaceutically acceptable" component is one that is suitable for use with humans and/or animals without undue adverse side effects (such as toxicity, irritation, and allergic response) commensurate with a reasonable benefit/risk ratio.

The term "stable" as used herein refers to the property of retaining at least a portion of the intended activity over a certain period of time.

The terms "mixture," "composition" and "formulation" as used herein refer to stable mixtures, compositions, and formulations, respectively. Preferred mixtures, compositions, and formulations are stable over a period of at least about three months.

Scar tissue may be formed as a result of injury or damage to the human body caused by a break in the skin. Such injury or damage may include cuts and bruises, or skin damage caused by infections, burns, scrapes, allergic reactions, acne, bites such as animal, human or insect, surgical incisions, and the like. Scar tissue forms as skin heals after an injury or surgery. The amount of scarring may be determined by the size, depth, and location of the wound, the age of the person, heredity, and skin characteristics such as skin pigmentation.

A keloid is an abnormal scar that is thicker, different color and texture, extends beyond the edge of the wound and has a tendency to recur. It often creates a thick, puckered effect simulating a tumor. Surgical repair may be necessary for this type of scar. A hypertrophic scar is characterized by an excessive amount of scar tissue in an incision or wound. It appears redder in color and firmer in texture than the surrounding skin and rises above it. The most common type of facial scarring is the result of acne infections and is referred to as an acne scar.

Massive injuries, such as burns, can cause a loss of a large area of skin and may form hypertrophic scars. Surgical repair may also be necessary for this type of scar.

The compositions and methods of the present invention may be topically applied to the scar tissue after the wound healing process is complete or may be applied to scar tissue formed by a partially completed wound healing process, wherein some scar tissue has formed but wound healing continues. In some cases, the methods and compositions of the present may provide an alternative to surgical repair of certain types of scars. In certain embodiments, the present invention may be limited to use on one or both of keloid scars and hypertrophic scars.

The compositions used in the method of the present invention for treatment of scar tissue include at least one flavonoid. Flavonoids are small organic compounds having a phenyl benzopyrone structure. They are found in the leaves, fruits, seeds, stems, or flowers of all vascular plants. Citrus fruits are a prominent source of flavonoids. On average, the daily Western diet contains about one gram of mixed flavonoids.

Examples of flavonoids include, without limitation, flavonones, flavanols, anthocyanidins, proanthocyanidins, procyanidolic oligomers, biflavans, polyphenols, rutinosides, hydroxyethylrutinosides, and leucoanthocyanins.

Suitable flavonoids for use in the present invention include those that do not induce significant, adverse side effects when topically administered to a patient in a therapeutically effective amount, and that do not react with any of the other ingredients of the composition used in the present invention to cause a substantial loss of activity of one or more compounds of the composition. Preferred flavonoids are obtained from natural sources. However, derivatives of such compounds may also be suitable for use in the present invention. Preferred flavonoids may be administered to humans without significant, adverse side effects when used in therapeutically effective amounts.

The selection of the flavonoid(s) included in the composition may be determined by factors such as toxicity, bioavailability, solubility or dispersability, and the like. Examples of flavonoids suitable for use in the present invention include, without limitation, (-)-epigallocatechin; (-)-epigallocatechin-gallate; 1,2,3,6-tetra-o-gallyol-β-d-glucose; 2'-o-acetylacetoside; 3,3',4-tri-o-methyl-ellagic acid; 6,3',4'-trihydroxy-5,7,8-trimethoxyflavone; 6-hydroxy-luteolin; 6-hydroxykaempferol-3,6-dimethyl ether; 7-o-acetyl-8-epiloganic acid; acacetin; acetoside; acetyl trisulfate quercetin; amentoflavone; apigenin; apiin; astragalin; avicularin; axillarin; baicalein; brazilin; brevifolin carboxylic acid; caryophyllene; catechin; chrysin; chrysin-5,7-dihydroxyflavone; chrysoeriol; chrysosplenol; chrysosplenoside-a; chrysosplenoside-d; cosmosiin; δ-cadinene; curcumin; cyanidin; dihydroquercetin; dimethylmussaenoside; diacerylcirsimaritin; diosmin; diosmetin; dosmetin; ellagic acid; ebinin; epicatechin; ethyl brevifolin carboxylate; flavocannibiside; flavosativaside; galangin; gallic acid; genistein; ginkgo flavone glycosides; ginkgo heterosides; gossypetin; gossypetin-8-glucoside; haematoxylin; hesperidine; hispiduloside; hyperin; indole; iridine; isoliquiritigenin; isoliquiritin; isoquercitrin; jionoside; juglanin; kaempferol; kaempferol-3-rhamnoside; kaempferol-3-neohesperidoside; kolaviron; licuraside; linariin; linarin; lonicerin; luteolin; luteolin-7-glucoside; luteolin-7-glucoronide; macrocarpal-a; macrocarpal-b; macrocarpal-d; macrocarpal-g; maniflavone; morin; methyl scutellarein; monoHER, diHER, triHER, tetraHER, myricetin; naringenin; naringin; nelumboside; nepetin; nepetrin; nerolidol; oligomeric proanthocyanidins; oxyayanin-a; pectolinarigenin; pectolinarin; pelargonidin; phloretin, phloridzin, polyphenols, including green tea polyphenols; quercetagetin; quercetin; quercimertrin; quercitrin; quercitryl-2" acetate; reynoutrin; rhamnetin; rhoifolin; rutin; scutellarein; sideritoflavone; silibin; silydianin; silychristine; silymarin; sophoricoside; sorbarin; spiraeoside; taxufolin; trifolin; vitexin; and wogonin, and the pharmaceutically acceptable salts; solvates; and derivatives of these compounds.

Preferred flavonoids are those that also have strong antioxidant properties. Examples of preferred flavonoids include, without limitation, (-)-epigallocatechin-3-gallate, catechin, rutin, quercetin, quercitrin, myricetin, kaempferol, myrecetrin luteolin, morin, fisetin, silymarin, apigenin, hesperitin, hesperidin, citrin, gossypetin, chrysin, oligomeric proanthocyanidins, biacalein, curcumin, gallic acid, epicatechin, dihydroquercetin, ginkgo flavone glycosides, ginkgo heterosides, silibin, silydianin silychristine, galangin, monoHER, diHER, triHER, tetraHER, naringenin, naringin, taxifolin, diosmin, phloretin, phloridzin, cyanidin, pelargonidin and derivatives thereof, and the pharmaceutically acceptable salts of these compounds.

More preferred flavonoids include, without limitation, quercetin, quercitrin, quercetin dihydrate, myricetin, rutin, kaempferol and myrecetrin. These compounds exhibit good antioxidant properties in combination with relatively low toxicity.

The amount of flavonoid employed in the compositions and methods may be sufficient to deliver a daily dosage of about 1 to about 150 mg/day to a patient. Alternatively, the formulation may deliver a daily dosage of about 10 to about 125 mg/day, or about 25 to about 100 mg/day to a patient. Optimum daily dosages may vary depending upon the particular flavonoid or mixture of flavonoids employed. The flavonoid component may make up from about 0.04 to about 2 wt % of the topical formulation, based on the total weight of the topical formulation.

Other compounds may also be included in the composition of the present invention to provide additional benefits when used in the method of the invention. DL-alpha lipoic acid, green tea extracts, preferably rich in catechins and polyphenols, vitamin A, vitamin $D_3$ and vitamin E, preferably in the form of vitamin E acetate.

When DL-alpha lipoic acid is employed, a suggested daily dosage is from about 0.2 mg/day to about 650 mg/day. When green tea extracts are employed, a suggested daily dosage is from about 0.1 mg/day to about 500 mg/day. When vitamin A is employed a suggested daily dosage is from about 0.05 to about 27.5 mg/day, and when vitamin $D_3$ is employed, a suggested daily dosage is from about 0.005 mg/day to about 1 mg/day. When vitamin E is employed as vitamin E acetate, a suggested daily dosage is from about 0.4 mg/day to about 500 mg/day. If other forms of these ingredients are employed, similar amounts of the active ingredient would be employed for the suggested daily dosage.

The compositions used in the present invention are preferably formulated with a pharmaceutically topical acceptable carrier. The non-carrier ingredients may be combined with the carrier materials to produce a particular dosage form, or be customized for a particular treatment regimen. Thus, the amount of each ingredient may vary depending on such factors as the particular mode of administration, the activity of the particular compounds employed, the age, bodyweight, general health, sex, and diet of the patient, time of administration, rate of excretion, the combination of compounds, or the severity of the scarring, among other potential factors. A standard reference text on pharmaceutical formulations, Remington's Pharmaceutical Sciences, 18th Ed., Mack Publishing Co. 1990, is hereby incorporated herein by reference in its entirety to provide further details on pharmaceutically acceptable topical carrier materials.

In the method of the invention, the composition is administered topically. The method includes the step of topically applying a composition, which includes a therapeutically effective amount of a flavonoid for the treatment of scar tissue, as defined above, and a pharmaceutically acceptable topical carrier, to existing scar tissue. In the method, an effective amount of the topical composition of the invention may be applied to the skin one to six times daily, as needed. The topical composition is applied directly to the scar tissue and/or to an area of the skin directly adjacent to the scar tissue.

More preferably, the topical composition of the present invention is applied to the skin at least once a day beginning after the formation of scar tissue, and preferably at least three times (e.g., morning, noon and bedtime) in a 24-hour period. For each application, it is preferable to apply an amount of the composition, which is sufficient to cover the scar tissue with a thin layer of the topical composition. The topical composition should preferably be rubbed into the skin until little or no residue remains on the skin.

A topical formulation of the composition used in the invention preferably includes a pharmaceutically acceptable topical carrier. Many pharmaceutically acceptable topical carriers are known to those of skill in the art. The compounds in the composition may be dissolved, dispersed and/or suspended in the topical carrier.

Exemplary topical carriers may include creams, ointments, lotions, pastes, jellies, sprays, aerosols, bath oils, and other topical pharmaceutical carriers, which accomplish direct contact between the active ingredients of the topical composition of the present invention and the pore of the skin. One type of pharmaceutically acceptable carrier is a hydrophilic ointment base. Suitable hydrophilic ointment bases are known to persons skilled in the art.

The pharmaceutically acceptable topical carrier may make up any amount of the composition, but typically makes up more than about 80%, and more preferably about 80-95% w/w of the total composition. Generally, it is recommended to formulate the compositions of the present invention on the basis of application of about 1 gram of the formulation per 2.54 cm of scar tissue, per day.

In one aspect, compositions of the invention may contain one or more citrus oils. It is believed that the terpenols present in citrus oil provide a beneficial effect in the present invention. Thus, citrus oils that have high contents of terpenols may be advantageously used in the present invention. Suitable citrus oils include orange oil, tangelo oil, tangerine oil, grapefruit oil, clementine oil, kumquat oil, mandarin orange oil, minneola oil and various types of lemon and lime oils.

One preferred citrus oil is tangerine oil (citrus reticulate) is an extract of tangerine peel. Tangerine oil contains a number of compounds including, for example,: α-pinene, myrcene, limonene, γ-terpinene, cirtronellal, linalool, neral, neryl acetate, gernayl acetate, geraniol, thymol and carvone. Limonene, a monocylic monoterpene, is a major constituent of tangerine oil. When tangerine oil is employed, a suggested dose range is from about 1 to about 535 mg/day. Tangerine oil (100% pure) may make up from about 0.16 to about 3 wt % of the topical formulation, based on the total weight of the topical formulation.

Another compound that may be included in the composition of the present invention is hyaluronic acid. Hyaluronic acid (alternatively spelled as hyaluronic acid) is a glycosamin-glycan composed of repeating disaccharide units of N-acetyl-glucosamine and D-glucuronic acid found in lubricating proteoglycans of synovial fluid, virtreous humor, cartilage, blood vessels and the umbilical cord. Retention of water is one of the biological functions of hyaluronic acid as well as providing nutrients and removing waste from cells that do not have a direct blood supply. When hyaluronic acid is employed, a suggested daily dose range is from about 1-10.5 mg/day to the patient, based on the use of pure hyaluronic acid. Hyaluronic acid may make up from about 0.3 to about 6 wt % of the topical formulation, based on the total weight of the topical formulation.

Another suitable topical carrier may be hydroxymethyl cellulose. Another suitable pharmaceutically acceptable carrier includes a solution of an acrylic copolymer in a non-aqueous solvent system. The non-aqueous solvent system preferably contains a polyethylene glycol such as, for example, methoxy polyethylene glycol 550 (MPEG). One preferred MPEG is Sentry Carbowax MPEG 550 (Dow Corp., Midland, Mich.), which is suitable for use in foods, pharmaceuticals, and cosmetics. The acrylic copolymer is preferably present in a concentration range of 3-6% by weight of solution. Also preferably, the acrylic copolymer has a molecular weight of more than 20,000. More preferably, the acrylic copolymer has a molecular weight of more than 100,000, to substantially prevent absorption of the acrylic copolymer by the human body through the skin.

Preferably, the pharmaceutically acceptable topical carrier independently provides benefits to the patient. For example, the topical carrier may comprise panthenol or a panthenol derivative. The panthenol derivatives useful in the present invention include at least D-panthenol, DL-panthenol, and mixtures thereof. Panthenol provides skin moisturizing properties, acts as a quick, deep penetrating component of the carrier, helps deliver the compounds through the skin to the area to be treated, and may impart a healing effect to damaged tissue. The amount of panthenol or panthenol derivative preferably ranges from 0.25 to 10 weight percent, more preferably from 0.5 to 5 weight percent, and, still more preferably, from 1 to 2 weight percent, based on the total weight of the topical composition.

Preferably, the topical carrier of the present invention contains at least a hydrophilic ointment base, panthenol or a panthenol derivative, and one or more dispersants, if needed to disperse an insoluble or partially insoluble compounds in the carrier.

The topical carrier of the present invention may also include additional ingredients such as other carriers, moisturizers, humectants, emollients, dispersants, radiation blocking compounds, particularly UV-blockers, as well as other suitable materials that do not have a significant adverse effect on the activity of the topical composition. Preferred additional ingredients for inclusion in the topical carrier are sodium acid phosphate moisturizer, witch hazel extract, glycerine humectant, apricot kernal oil emollient, Ajidew NL NaPCA, ascorbyl palmitate, and corn oil dispersant.

As noted above, dosages may vary with the manner of formulating the compounds. The appropriate unit dosage may be determined by dividing the daily dosage by the number of unit doses per day. The flavonoid of the present invention is administered in a therapeutically effective amount.

The following examples are provided to describe the invention in further detail. These examples, which set forth a preferred mode presently contemplated for carrying out the invention, are intended to illustrate and not to limit the invention.

EXAMPLES 1-2 AND COMPARATIVE EXAMPLES A-B

In this example, a double-blind randomized, single center, placebo-controlled study was conducted to evaluate the cosmetic effect of compositions and methods of the present invention on surgical scar appearance.

The study recruited a total of 60 subjects, 18 years of age or older, who were randomized into a 12-week study. Subjects were eligible to participate in the study if they met the following criteria:

(1) Subjects muse present with surgical scar(s) immediately following suture removal 7 to 14 days after surgery, and
(2) Scar(s) must be between 5 and 30 cm in length, Subjects were randomly assigned one of four possible treatments:
1. The composition of Example 1 (20 subjects),
2. The composition of Example 2 (20 subjects),
3. Mederma®, a commercially available scar cream (Comparative Example A) (10 subjects), or
4. placebo (Comparative Example B) (10 subjects).

Subjects were instructed to evenly apply a small amount of the topical cream three (3) times a day for twelve (12) weeks. The topical cream was applied using their finger and was gently and thoroughly rubbed into the scar and the immediate surrounding area. All participants were instructed not to apply the topical cream on an open wound or directly over a steri-strip. If a steri-strip was present on the scar, the topical cream was applied around and not directly on the steri-strip.

At baseline (visit 1), and at visits 2, 3, 4, 5, and 6 (1, 2, 4, 8 and 12 weeks of treatment), participants completed a self-assessment questionnaire, which solicited quality of life information on: importance of healing of the scar, how noticeable they felt it was and if the appearance of the scar made them feel self conscious.

At baseline and at visits 2, 3, 4, 5, and 6 (1, 2, 4, 8 and 12 weeks of treatment), a Clinician's Assessment of the Scar and a 10-point Scar Scale Evaluation (10 being the best, 0 being the worst) was completed. The Clinician's Assessment of the Scar included questions about the type of sutures used to close the skin, type of surgery, length and width of scar, color and condition of scar and surrounding skin area, use of bandage or steri-strips, and the effect of scar on quality of life. In addition, at each visit, a controlled photograph of the scar was taken to aide the investigator in the Scar Scale Evaluation and to visually document the progress of scar appearance.

The primary endpoint of this study was to determine the cosmetic effect on scar appearance. Efficacy was based on the following endpoints: Subject's self-assessment of the scar's appearance, clinician's assessment of the scar's appearance, including photography of the scar, and 10 point Scar Scale Evaluation scores.

Efficacy was assessed on the basis of the subject's Assessment of Scar questionnaire completed by the subject at baseline, and at 1, 2, 4, 8 and 12 weeks of treatment. The Clinician's Assessment of Scar questionnaire was completed by the Investigator at 1, 2, 4, 8 and 12 weeks of treatment. Scar Scale Evaluation scores were completed by the Investigator at baseline, 1, 2, 4, 8, and 12 weeks of treatment.

The materials of Examples 1-2 and Comparative Example B were blended under ambient conditions without any specific protocol or procedure. The formulations of the compositions are given in Table 1.

TABLE 1

| Component | Example 1 | Example 2 | Comparative Example B (Placebo) |
|---|---|---|---|
| hydrophilic ointment base (non-USP) | 94.7 wt % | 87.56 | 95.3 wt % |
| quercetin dihydrate | 0.4 wt % | 0.385 | N/a |
| tangerine oil, 100% pure | 1.6 wt % | N/a | 1.6 wt % |
| hyaluronic acid, 100% pure (1% aqueous solution) | 3.1 wt % | N/a | 3.1 wt % |
| Ajidew NL-50 NaPCA | N/a | 4.821 | N/a |
| DL-Panthenol | N/a | 0.964 | N/a |
| Glycerin | N/a | 0.964 | N/a |
| Apricot Kernal Oil | N/a | 0.578 | N/a |

TABLE 1-continued

| Component | Example 1 | Example 2 | Comparative Example B (Placebo) |
|---|---|---|---|
| Vitamins A and $D_3$ in corn oil | N/a | 1.157 | N/a |
| Witch Hazel extract | N/a | 2.314 | N/a |
| Vitamin E acetate | N/a | 0.385 | N/a |
| Ascorbyl Palmitate | N/a | 0.385 | N/a |
| Green Tea 36–50% C&P | N/a | 0.0964 | N/a |

The mean scar length of all subjects of each study group is given below in Table 2.

TABLE 2

| Time of Measurement | Example 1 | Example 2 | Comparative Example A | Comparative Example B |
|---|---|---|---|---|
| Baseline | 12.67 cm | 7.88 cm | 8.15 cm | 8.3 cm |
| 12 weeks | 11.6 cm | 7.73 cm | 6.13 cm | 7.73 cm |

Tables 3-6 below summarize the results of the study.

TABLE 3

Percent reduction in scar area.

| | |
|---|---|
| Example 1 | 47.3% |
| Example 2 | 43.3% |
| Comparative Example A | 19.6% |

TABLE 4

Scar Width Change at Visit 5 (8 weeks of treatment)

| Treatment Group | Mean Scar Width Change (cm) |
|---|---|
| Example 1 | −0.2025 |
| Example 2 | −0.2140 |
| Comparative Example A | +0.1000 |
| Comparative Example B | −0.0350 |

TABLE 5

Scar Width Change at Visit 6 (12 weeks of treatment)

| Treatment Group | Mean Scar Width Change (cm) |
|---|---|
| Example 1 | −0.1830 |
| Example 2 | −0.1900 |
| Comparative Example A | −0.0517 |
| Comparative Example B | −0.1000 |

TABLE 6

Scar Area Change at Visit 5 (8 weeks of treatment)

| Treatment Group | Mean Scar Area Change ($cm^2$) |
|---|---|
| Example 1 | −3.765 |
| Example 2 | −2.687 |
| Comparative Example A | −0.775 |
| Comparative Example B | −0.567 |

TABLE 7

Scar Area Change at Visit 6 (12 weeks of treatment)

| Treatment Group | Mean Scar Area Change (cm$^2$) |
| --- | --- |
| Example 1 | −3.621 |
| Example 2 | −2.234 |
| Comparative Example A | −1.140 |
| Comparative Example B | −0.450 |

TABLE 8

Scar Area Percent Change at Visit 5 (8 weeks of treatment)

| Treatment Group | Mean Scar Area Percent Change |
| --- | --- |
| Example 1 | −61.84 |
| Example 2 | −46.72 |
| Comparative Example A | +106.94 |
| Comparative Example B | +28.61 |

TABLE 9

Scar Area Percent Change at Visit 6 (12 weeks of treatment)

| Treatment Group | Mean Scar Area Percent Change |
| --- | --- |
| Example 1 | −47.26 |
| Example 2 | −47.6 |
| Comparative Example A | +11.27 |
| Comparative Example B | +11.11 |

Each of Tables 3-9 show improvement in scar tissue reduction for the compositions of Examples 1-2, relative to Mederma® and placebo.

The mean scar scale evaluation was conduced using the following Scar Scale.

SCAR SCALE

10- No visible scar, no evidence of discoloration, irritation, edema, or dehiscence. Skin is radiant and smooth.
9- Very slight pinkness, scar is not visible at a glance, no visible edema, flat in appearance, no skin irritation or dehiscence present, scar area is hydrated and firm.
8- Flat, light pink tone, none or very little edema, very little irritation and/or dehiscence, and scar area is smooth and energized.
7- Very slightly noticeable scar, pink tone, slight edema, slight irritation and/or dehiscence, and slightly firm.
6- Slightly noticeable scar, flatter, bright pink discoloration, mild edema, mild irritation and/or dehiscence, slightly hydrated and energized.
5- Noticeable scar, pinkish-red discoloration, slight edema, slight irritation and/or dehiscence, scar area becoming softer and hydrated.
4- Mildly noticeable from a distance, light red discoloration, mild to moderate edema, mild to moderate irritation and/or moderate dehiscence.
3- Noticeable from a distance, red discoloration, moderate edema, moderate irritation and/or moderate dehiscence.
2- Very noticeable from a distance, shiny red discoloration, moderate to severe edema, moderate to severe irritation and/or moderate to severe dehiscence.
1- Moderately noticeable from a distance, bright red coloring, severe edema, severe irritation and/or severe dehiscence.
0- Severely noticeable and distinct scar, very bright red coloring, very severe edema, very severe irritation, and/or very severe dehiscence.

TABLE 10

Mean Scar Scale Evaluation

| Treatment Group | Mean Scar Scale Evaluation |
| --- | --- |
| Example 1 | 4.91 |
| Example 2 | 3.09 |
| Comparative Example A | 4.43 |
| Comparative Example B | 5.50 |

These results show that the formulation of Example 1 reduced the amount of scar tissue that had formed post surgery. Clinicians assessments showed that Example 1 proves better than the commercially available Mederma® scar crea, in overall treatment of post surgical scar tissue.

Although the present invention has been described and exemplified in terms of certain preferred embodiments, other embodiments will be apparent to those skilled in the art. The invention is, therefore, not limited to the particular embodiments described and exemplified, but is capable of modification or variation. The full scope of the invention is delineated by the appended claims.

What is claimed is:

1. A method for reduction of scar tissue or improving the appearance of scar tissue comprising the step of topically applying to scar tissue an effective amount of a composition to reduce or improve the appearance of the scar tissue which comprises a therapeutically effective amount of one or more flavonoids.

2. The method of claim 1, wherein the flavonoid is selected from the group consisting of (-)-epigallocatechin; (-)-epigallocatechin-gallate; 1,2,3,6-tetra-o-gallyol-β-d-glucose; 2' o-acetylacetoside; 3,3',4-tri-o-methyl-ellagic acid; 6,3',4'-trihydroxy-5,7,8-trimethoxyflavone; 6-hydroxy-luteolin; 6-hydroxykaempferol-3,6-dimethyl ether; 7-o-acetyl-8-epi-loganic acid; acacetin; acetoside; acetyl trisulfate quercetin; amentoflavone; apigenin; apiin; astragalin; avicularin; axillarin; baicalein; brazilin; brevifolin carboxylic acid; caryophyllene; catechin; chrysin; chrysin-5,7-dihydroxyflavone; chrysoeriol; chrysosplenol; chrysosplenoside-a; chrysosplenoside-d; cosmosiin; δ-cadinene; curcumin; dihydroquercetin; dimethylmussaenoside; diacerylcirsimaritin; diosmetin; dosmetin; ellagic acid; ebinin; epicatechin; ethyl brevifolin carboxylate; flavocannibiside; flavosativaside; gallic acid; genistein; ginkgo flavone glycosides; ginkgo heterosides; gossypetin; gossypetin-8-glucosidc; haematoxylin; hesperidine; hispiduloside; hyperin; indole; iridine; isoliquiritigenin; isoliquiritin; isoquercitrin; j ionoside; juglanin; kaempferol; kaempferol-3-rhamnoside; kaempferol-3-neohesperidoside; kolaviron; licuraside; linariin; linarin; lonicerin; luteolin; luetolin-7-glucoside; luteolin-7-glucoside; luetolin-7-glucoronide; macrocarpal-a; macrocarpal-b; macrocarpal-d; macrocarpal-g; maniflavone; morin; methyl scutellarein; myricetin; naringenin; naringin; nelumboside; nepetin; nepetrin; nerolidol; oligomeric proanthocyanidins; oxyayanin-a; pectolinarigenin; pectolinarin; polyphenols; quercetagetin; quercetin; quercimertrin; quercitrin; quercitryl-2" acetate; reynoutrin; rhamnetin; rhoifolin; rutin; scutellarein; sideritoflavone; silibin; silydianin; silychristinc; silymarin; sophoricoside; sorbarin; spiraeoside; trifolin; vitexin; and wogonin; and pharmaceutically acceptable salts thereof.

3. The method of claim 1, wherein the flavonoid is selected from the group consisting of (-)-epigallocatechin-3-gallate, catechin, rutin, quercetin, quercitrin, myricetin, kaempferol, myrecetrin luteolin, morin, fisetin, silymarin, apigenin, hesperitin, citrin, gossypetin, chrysin, oligomeric proanthocyanidins, polyphenols, biacalein, curcumin, gallic acid, epicatechin, dihydroquercetin, ginkgo flavone glycosides, ginkgo heterosides, silibin, silydianin silychristine, and pharmaceutically acceptable salts thereof.

4. The method of claim 1, wherein the flavonoid is selected from the group consisting of quercetin, quercitrin, quercetin dihydrate, myricetin, rutin, kaempferol, myrecetrin, galangin, monoHER, diHER, triHER, tetraHER, naringenin, naringin, taxifolin, diosmin, phloretin, phloridzin, cyanidin, pelargonidin and pharmaceutically acceptable salts thereof.

5. The method of claim 1, further comprising a pharmaceutically acceptable topical carrier.

6. The method of claim 5, wherein the pharmaceutically acceptable topical carrier comprises hyalauronic acid.

7. The method of claim 6 wherein the pharmaceutically acceptable topical carrier comprises tangerine oil.

8. The method as claimed in claim 7, wherein the pharmaceutically acceptable carrier comprises a sufficient amount of at least one non-U.S.P. hydrophilic ointment base to form a substantially topical composition.

9. The method as claimed in claim 8, wherein the pharmaceutically acceptable carrier further comprises a sufficient amount of a panthenol selected from D-panthenol and DL-panthenol to promote penetration of one or more compounds of the composition into the skin.

10. The method of claim 1, wherein the flavonoid comprises from about 0.04 to about 2.0 wt % of the composition, based on the total weight of the composition.

11. The method of claim 1, wherein a daily dose of the composition comprises from about 1 to about 150 mg of flavonoid, per day.

12. The method of claim 1, wherein the composition further comprises green tea extract.

13. The method of claim 12, wherein the composition further comprises rutin.

14. The method of claim 13, wherein the composition further comprises DL-alpha lipoic acid.

* * * * *

UNITED STATES PATENT AND TRADEMARK OFFICE
CERTIFICATE OF CORRECTION

| | |
|---|---|
| PATENT NO. | : 7,399,783 B2 |
| APPLICATION NO. | : 11/158986 |
| DATED | : July 15, 2008 |
| INVENTOR(S) | : Richard A. Rosenbloom |

Page 1 of 1

It is certified that error appears in the above-identified patent and that said Letters Patent is hereby corrected as shown below:

Column 2, line 58, replace "bums" with --burns--, and

Column 10, claim 2, line 19 replace "j ionoside" with --jionoside--, no space.

Signed and Sealed this

Sixteenth Day of September, 2008

JON W. DUDAS
*Director of the United States Patent and Trademark Office*